(12) United States Patent
Singh et al.

(10) Patent No.: US 10,390,902 B2
(45) Date of Patent: Aug. 27, 2019

(54) SYSTEM AND METHOD FOR INSTRUMENT TRACKING

(71) Applicant: HCL TECHNOLOGIES LIMITED, Noida, Uttar Pradesh (IN)

(72) Inventors: Lalit Kumar Singh, Uttar Pradesh (IN); Pankaj Gupta, Uttar Pradesh (IN)

(73) Assignee: HCL TECHNOLOGIES LIMITED (IN)

(*) Notice: Subject to any disclaimer, the term of this patent is extended or adjusted under 35 U.S.C. 154(b) by 0 days.

(21) Appl. No.: 16/010,285

(22) Filed: Jun. 15, 2018

(65) Prior Publication Data

US 2019/0000586 A1 Jan. 3, 2019

(30) Foreign Application Priority Data

Jun. 29, 2017 (IN) .............................. 201711022810

(51) Int. Cl.
*A61B 90/00* (2016.01)
*G08B 21/24* (2006.01)
*A61B 90/98* (2016.01)
*A61B 34/20* (2016.01)
(Continued)

(52) U.S. Cl.
CPC .............. *A61B 90/08* (2016.02); *A61B 34/20* (2016.02); *A61B 90/98* (2016.02); *G08B 21/24* (2013.01); *A61B 50/31* (2016.02); *A61B 2050/311* (2016.02); *A61B 2090/0803* (2016.02); *A61B 2090/0804* (2016.02); *A61B 2090/0805* (2016.02); *H04N 5/33* (2013.01)

(58) Field of Classification Search
CPC ........................ A61B 34/20; A61B 2034/2048
USPC .................. 340/568.1, 539.1, 539.13, 539.32
See application file for complete search history.

(56) References Cited

U.S. PATENT DOCUMENTS 4,974,166 A 11/1990 Maney et al.
5,374,813 A * 12/1994 Shipp ..................... G06Q 10/08
235/375
(Continued)

FOREIGN PATENT DOCUMENTS

WO WO-9527252 A1 * 10/1995 ........... G06Q 10/087

OTHER PUBLICATIONS

Wei Liu, Hongliang Ren "Cognitive tracking of surgical instruments based on stereo vision and depth sensing" Dec. 12-14, 2013.
(Continued)

*Primary Examiner* — Emily C Terrell
(74) *Attorney, Agent, or Firm* — Hayes Soloway P.C.

(57) ABSTRACT

Disclosed is a device and method for tracking one or more instrument in a surgical kit. The method comprises receiving one or more signals from a first set of sensors and activating a second set of sensors based on the one or more signals. Further to activating, the method comprises receiving data from the second set of sensors and computing, a current state associated with each of the instrument based on the data, and historical data. Furthermore, the method comprises transmitting the current state of the surgical kit, the current state associated with each of the instrument and a location co-ordinate of the surgical kit via a communication channel based on a signal strength of the communication channel and deactivating the tracking device, thereby tracking one or more instrument in a surgical kit.

10 Claims, 4 Drawing Sheets

(51) Int. Cl.
 A61B 50/31 (2016.01)
 H04N 5/33 (2006.01)

(56) References Cited

U.S. PATENT DOCUMENTS

| | | | | |
|---|---|---|---|---|
| 5,671,362 | A * | 9/1997 | Cowe | G06Q 10/087 340/5.92 |
| 7,118,029 | B2 | 10/2006 | Nycz et al. | |
| 7,362,228 | B2 | 4/2008 | Nycz et al. | |
| 7,518,502 | B2 | 4/2009 | Austin et al. | |
| 8,659,420 | B2 | 2/2014 | Salvat, Jr. | |
| 2003/0078693 | A1* | 4/2003 | Chavez | G06Q 10/087 700/237 |
| 2006/0145856 | A1 | 7/2006 | Tethrake et al. | |
| 2008/0030345 | A1* | 2/2008 | Austin | A61B 90/90 340/572.8 |
| 2015/0272575 | A1* | 10/2015 | Leimbach | A61B 17/072 227/175.3 |

OTHER PUBLICATIONS

Allison Okamura "Tracking for surgical navigation" 2016.

* cited by examiner

SYSTEM AND METHOD FOR INSTRUMENT TRACKING

CROSS-REFERENCE TO RELATED APPLICATIONS AND PRIORITY

This present application claims benefit from Indian Complete Patent Application No 201711022810 filed on 29 Jun. 2018, the entirety of which is hereby incorporated by reference.

TECHNICAL FIELD

The present subject matter described herein, in general, relates to a device and a method for tracking, and more particularly a device and a method for enabling tracking one or more instrument in a surgical kit.

BACKGROUND

Generally, a tracking system is used for the observing of objects on the move and supplying a timely ordered sequence of respective location data to a user. Particularly in distribution and logistics of many types of products, track and trace or tracking and tracing, concerns a process of determining the current and past locations and other information of a unique item or property.

Now a day there are many tracking systems available in the market, for example a bar code, gate, Global Positioning Systems, bar-code systems, automatic identification (RFID auto-id). However, such conventional tracking systems fail when utilized in the healthcare domain. Generally, hospitals and surgical kit providers across the country utilized conventional tracking system in order to track a variety of assets, including everything from wheelchairs to IV pumps, and various types of surgical kits. In particular, conventional tracking systems implements on surgical tools fail, because these the surgical tools are regularly put through a harsh sterilization process involving intense heat and significant moisture. Further, the conventional tracking systems consume a substantial amount of battery for tracking resulting in frequent battery change.

Before the present a device and a method for enabling tracking one or more instrument in a surgical kit, are described, it is to be understood that this application is not limited to the particular device, systems, and methodologies described, as there can be multiple possible embodiments which are not expressly illustrated in the present disclosures. It is also to be understood that the terminology used in the description is for the purpose of describing the particular implementations or versions or embodiments only, and is not intended to limit the scope of the present application. This summary is provided to introduce aspects related to a device and a method for tracking one or more instrument in a surgical kit. This summary is not intended to identify essential features of the claimed subject matter nor is it intended for use in determining or limiting the scope of the claimed subject matter.

In one implementation, a device for tracking one or more instrument in a surgical kit is disclosed. In one aspect, the device comprises a memory and a machine control unit coupled to the memory. Further, the machine control unit may be capable of executing instructions in the memory to perform one or more steps. In the aspect, the machine control unit may receive one or more signals from a first set of sensors and activate a second set of sensor based on the one or more signals. In one example, the first set of sensors may be configured to transmit the one or more signals upon detecting change in a state of the surgical kit. In one other example, the state may be one of an open state and a closed state. In another example, the first set of sensors may comprises one or more of a magnetic sensor, and a motion sensor and the second set of sensors may comprise one or more of a load cell, a Piezo sensors, an infrared sensor, and a camera. Further to activating, the machine control unit may receive data from the second set of sensors, and compute a current state associated with each of the instrument based on the data, and historical data. In one example, the data may be associated with one or more instruments within the surgical kit. Upon computing, the machine control unit may transmit the current state of the surgical kit, the current state associated with each of the instrument and a location co-ordinate of the surgical kit via a communication channel based on a signal strength of the communication channel and deactivate the second set of sensors, thereby tracking one or more instrument in a surgical kit.

In one implementation, a method for tracking one or more instrument in a surgical kit is disclosed. In one aspect, the method may comprise receiving one or more signals from a first set of sensors and activating a second set of sensor based on the one or more signals. In example, the first set of sensors may be configured to transmit the one or more signals upon detecting change in a state of the surgical kit and the state may be one of an open state and a closed state. In another example, the first set of sensors may comprise one or more of a magnetic sensor, and a motion sensor; and the second set of sensors may comprise one or more of a load cell, a Piezo sensor, an infrared sensor, and a camera. The method further comprises receiving data from the second set of sensors and computing a current state associated with each of the instrument based on the data, and historical data. In one example, the data may be associated with one or more instruments within the surgical kit. The method furthermore comprises transmitting the current state of the surgical kit, the current state associated with each of the instrument and a location co-ordinate of the surgical kit via a communication channel based on a signal strength of the communication channel and deactivating the second set of sensors, thereby tracking one or more instrument in a surgical kit.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures; however, the invention is not limited to the specific method and system disclosed in the document and the figures.

The present subject matter is described detail with reference to the accompanying figures. In the figures, the left-most digit(s) of a reference number identifies the figure in which the reference number first appears. The same numbers are used throughout the drawings to refer various features of the present subject matter.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any a device and a method for enabling tracking one or more instrument in a surgical kit, similar or equivalent to those described herein can be used in the practice or testing of embodiments of the present disclosure, the exemplary, a device and a method for enabling tracking one or more instrument in a surgical kit are now described. The disclosed embodiments for enabling tracking one or more instrument in a surgical kit are merely examples of the disclosure, which may be embodied in various forms.

Various modifications to the embodiment will be readily apparent to those skilled in the art and the generic principles herein may be applied to other embodiments for tracking one or more instrument in a surgical kit. However, one of ordinary skill in the art will readily recognize that the present disclosure for tracking one or more instrument in a surgical kit is not intended to be limited to the embodiments described, but is to be accorded the widest scope consistent with the principles and features described herein.

In one implementation, a device and method for tracking one or more instrument in a surgical kit, is described. In the embodiment, the device may comprise a first set of sensors a second set of sensors, and a machine control unit electronically coupled to the first set of sensors and the second set of sensors. In another example, the first set of sensors may comprise one or more of a magnetic sensor, and a motion sensor; and the second set of sensors may comprise one or more of a load cell, a Piezo sensor, an infrared sensor, and a camera.

In the embodiment, the first set of sensors may be configured to transmit one or more signals upon detecting change in state of the surgical kit. In one example, the state of surgical kit may be one of an open slate and a closes state. In one other example, the first set of sensors may be configured transmit one or more signals after a predefined time interval, such as five min, upon detecting change in state of the surgical kit. In the example, the change in state may be from open state to closed state or from closed state to open state. Further, in the embodiment, the second set of sensors may be configured to transmit data associated with one or more instruments within surgical kit.

Furthermore, in the embodiment, the machine control unit may be configured to receiving one or more signals from the first set of sensors and activate the second set of sensor based on the one or more signals. Further to activating, the machine control unit may be configured to receive data from the second set of sensors and compute a current state associated with each of the instrument based on the data, and historical data. Upon computing, the machine control unit may be configured to transmit the current state of the surgical kit, the current state associated with each of the instrument and a location co-ordinate of the surgical kit via a communication channel based on a signal strength of the communication channel and deactivate the second set of sensor, thereby tracking one or more instrument in a surgical kit.

Figure 1:
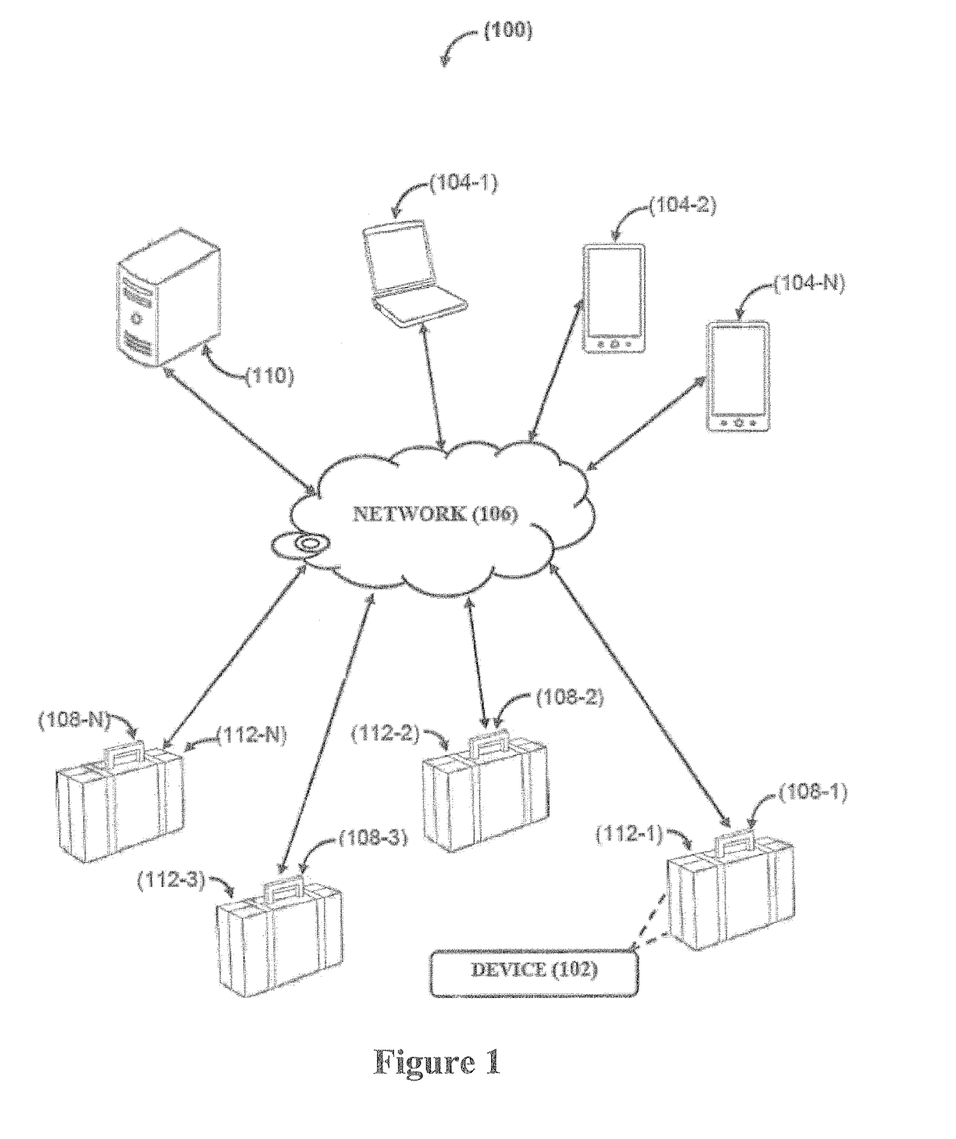
FIG. 1 illustrates a network implementation of a device for tracking one or more instrument in a surgical kit, in accordance with an embodiment of the present subject matter.
Figure 2:
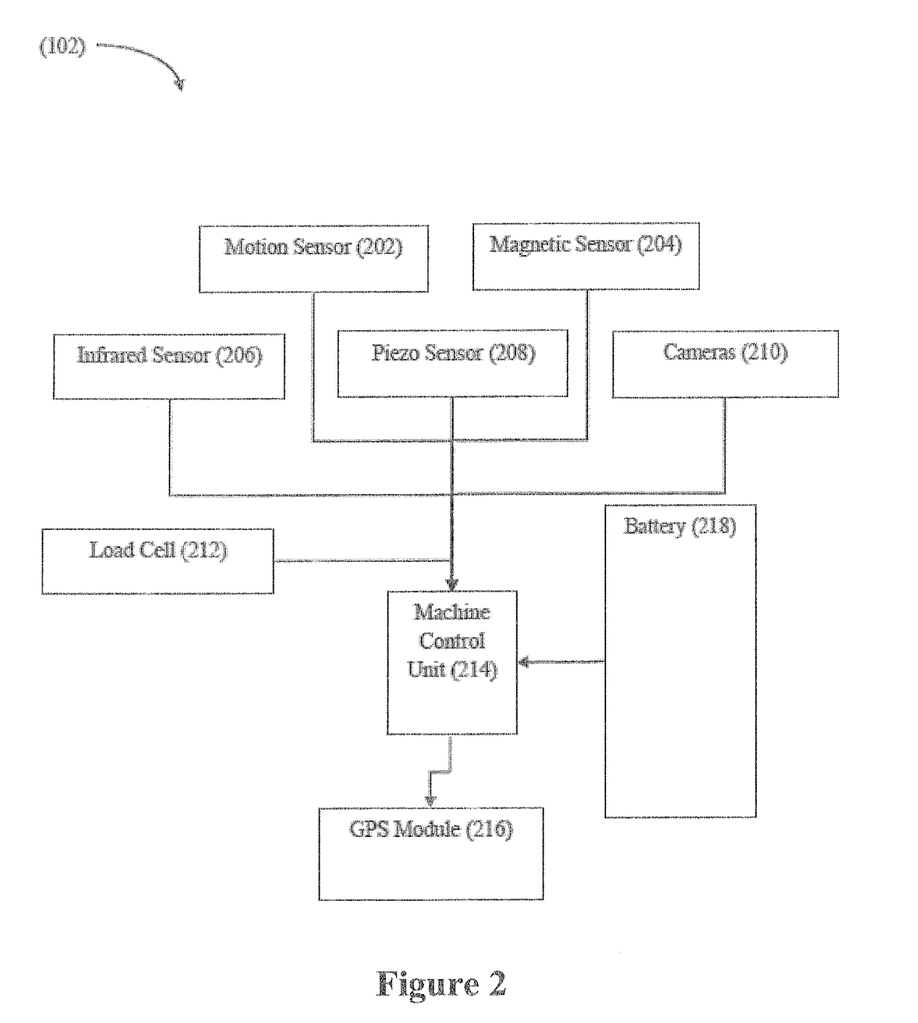
FIG. 2 illustrates a circuit diagram of the device for tracking one or more instrument in a surgical kit, in accordance with an embodiment of the present subject matter.

Referring now to FIG. 1, a network implementation 100 of a device 102 for tracking one or more instrument in a surgical kit 112-1, 112-2, 112-3 . . . 112-N, in accordance with an embodiment of the present subject matter may be described. Referring now to FIG. 2, a circuit diagram of the device 102 for tracking one or more instrument in a surgical kit 112-1, 112-2, 112-3 . . . 112-N, in accordance with an embodiment of the present subject matter may be described.

In one embodiment, the present subject matter is explained considering that the device(s) 102 implemented on the surgical kits 112-1, 112-2, 112-3 . . . 112-N, herein after jointly and individually referred to as the surgical kit 112. In one example, the device 102 may be implemented as a device 102 connected to the network 106. It may also be understood that the device 102 supports a plurality of browsers and all viewports. Examples of the plurality of browsers may include, but not limited to, Chrome™, Mozilla™, Internet Explorer™, Safari™, and Opera™. It will also be understood that the device 102 may be accessed by multiple users through one or more user devices 104. In one example, the user device 104 may be a laptop, a mobile, a smartphone, desktop computer and the like. Furthermore, the device 102 may be communicatively coupled to one or more database for storing data and one or more servers 110 for transmitting data. In one example, the database may be any of the relationship database and the like. Further the device installed on the surgical kit 112 may be communicatively coupled to the one or more user devices 104, the database, and the server 110 via communication channel, herein after referred to as a network 106.

In one implementation, the network 106 may be a wireless network, a wired network or a combination thereof. The network 106 can be implemented as one of the different types of networks, such as intranet, local area network (LAN), Wireless Personal Area Network (WPAN), Wireless Local Area Network (WLAN), wide area network (WAN), the internet, and the like. The network 106 may be either a dedicated network or a shared network. The shared network represents an association of the different types of networks that use a variety of protocols, for example, MQ Telemetry Transport (MQTT), Extensible Messaging and Presence Protocol (XMPP), Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In the embodiment, the device 102 for tracking one or more instrument in a surgical kit 112-1, 112-2, 112-3 . . . 112-N, in accordance with an embodiment of the present subject matter may be described. In the embodiment, the device 102 may comprise a first set of sensors a second set of sensors and a machine control unit 214 electronically coupled to the first set of sensors and the second set of sensors. In another example, the first set of sensors may comprise one or more of a magnetic sensor 204, and a motion sensor 202; and the second set of sensors may comprise one or more of a load cell 212, a Piezo sensor 208, an infrared sensor 206, and a camera 210.

In the embodiment, the first set of sensors may be configured to transmit one or more signals upon detecting change in state of the surgical kit 112. In one example, the state of surgical kit 113 may be one of an open state and a closes state. In one other example, the first set of sensors may be configured transmit one or more signals after a predefined time interval, such as five min, upon detecting change in state of the surgical kit 112. In the example, the change in state may be from open state to closed state or from closed state to open state. Further, in the embodiment, the second set of sensors may be configured to transmit data associated with one or more instruments within surgical kit 112.

Furthermore, in the embodiment, the machine control unit 214 may be configured to receiving one or more signals from the first set of sensors and activate the second set of sensor based on the one or more signals. Further to activating, the machine control unit 214 may be configured to receive data from the second set of sensors and compute a current state associated with each of the instrument based on the data, and historical data. Upon computing, the machine control unit 214 may be configured to transmit the current state of the surgical kit, the current state associated with each of the instrument and a location co-ordinate of the surgical kit via a communication channel 216 based on a signal strength of the communication channel 216 and deactivate the second set of sensor, thereby tracking one or more instrument in a surgical kit 112.

Figure 3:
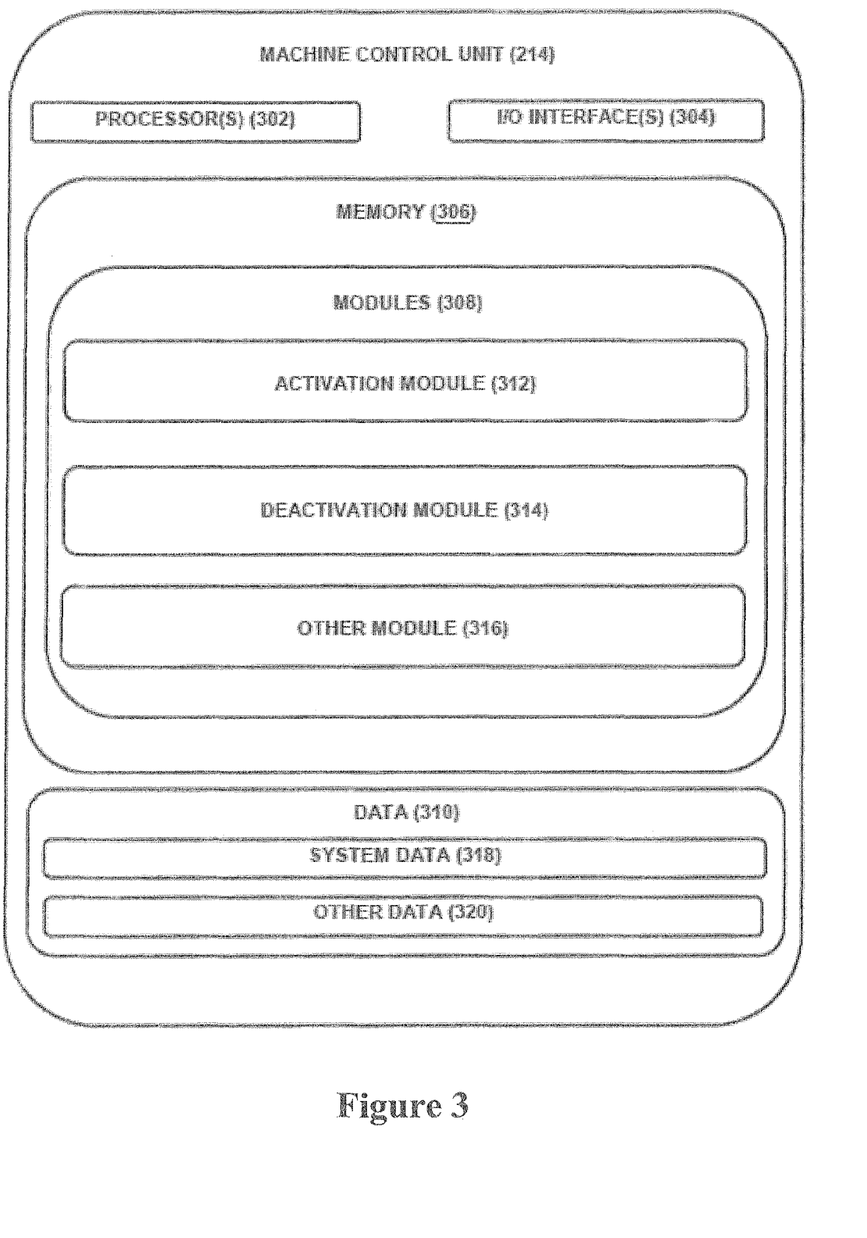
FIG. 3 illustrates the machine control unit and its subcomponents for tracking one or more instrument in a surgical kit, in accordance with an embodiment of the present subject matter.

Referring now to FIG. 3, the machine control unit 214 is illustrated in accordance with an embodiment of the present subject matter. In one embodiment, the machine control unit 214 may include at least one processor 302, an input/output (I/O) interface 304, and a memory 306. The at least one processor 302 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 may be configured to fetch and execute computer-readable instructions stored in the memory 206.

The I/O interface 304 may include a variety of software and hardware interfaces, for example, a web interface, a graphical user interface, and the like. The I/O interface 304 may allow the machine control unit 214 to interact with the user directly or through the user devices 104. Further, the I/O interface 304 may enable the machine control unit 214 to communicate with other computing devices, such as web servers and external data servers (not shown). The I/O interface 304 can facilitate multiple communications within a wide variety of networks and protocol types, including wired networks, for example, LAN, cable, etc., and wireless networks, such as WLAN, cellular, or satellite. The I/O interface 304 may include one or more ports for connecting a number of devices to one another or to another server.

The memory 306 may include any computer-readable medium or computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 306 may include modules 308 and data 310.

The modules 308 include routines, programs, objects, components, data structures, etc., which perform particular tasks or implement particular abstract data types. In one implementation, the modules 308 may include an activation module 312, a deactivation module 314 and other module 218. The other modules 318 may include programs or coded instructions that supplement applications and functions of the machine control unit 214. The modules 308 described herein may be implemented as software modules that may be executed in the cloud-based computing environment of the machine control unit 214.

The memory 306, amongst other things, serves as a repository for storing data processed, received, and generated by one or more of the modules 308. The memory 306 may include data generated as a result of the execution of one or more modules in the other module 320. In one implementation, the memory may include data 310. Further, the data 310 may include a system data 320 for storing data processed, computed received and generated by one or more of the modules 308. Furthermore, the data 310 may include other data 322 for storing data generated as a result of the execution of one or more modules in the other module 318.

In one implementation, at first, a user may use the user device 104 to access the device 102 and in turn the machine control unit 214. The user may register using the I/O interface 204 in order to use the device 102. In one aspect, the user may access the I/O interface 204 of the device 102 for obtaining information or providing input information. In one other embodiment, the user may user the user device 104 to register at a central server in order to obtain or receive data from or about the device 102 and the surgical kit. In one implementation, the device 102 utilizing the machine control unit 214 may automatically provide information to the user through I/O interface 304, and user device 104. In one embodiment, the machine control unit 214 may comprises an activation module 312 and deactivation module 314 for performing one or more instructions.

In one embodiment, the activation module 312 may receive one or more signals from a first set of sensors and activate a second set of sensor based on the one or more signals. In one example, the first set of sensors may comprise one or more of a magnetic sensor 202, and a motion sensor 204 and the second set of sensors comprises one or more of a load cell 212, a Piezo sensor 208, an infrared sensor 206, and a camera 210. In one more example, the piezo sensor 208 may be configured for heavy instruments and infrared sensors 206 may be configured for light instruments. In one other example, the first set of sensors may be configured to transmit the one or more signals upon detecting change in a state of the surgical kit such as an open state and a closed state. In example, open state may be understood as the state were the surgical kit is open and closed state may be understood as the state were the surgical kit is closed.

In the embodiment, the deactivation module 314 may receive data from the second set of sensors and compute a current state associated with each of the instrument based on the data and historical data. In one example, the data may be associated with one or more instruments within the surgical kit. In one other example, the data may comprise one of load data form the load cell 212, image data form the camera 210, and a signal from the infrared sensor 206 and the piezo sensor 208. In one example the historical data may comprises the last status of the instruments within the surgical kit 112. In the embodiment, the current state may be instrument present in the surgical kit and instrument absent in the surgical kit. In the one example, the current state may be instrument such as needle or syringe, present in reduce quantity. In the example, the deactivation module 316 may compute the reduction based on analysis of current load cell data and historical load cell data. In one other embodiment, the deactivation module 316 may compute a total usage time of the instrument based on the current state and the historical data.

In the embodiment, further to computing, the deactivation module may transmit both the data and the computed data such as the current state of the surgical kit and a location co-ordinate of the surgical kit via a communication channel based on a signal strength of the communication channel and deactivate the second set of sensor, thereby tracking one or more instrument in a surgical kit. In one other embodiment, the deactivation module 316 may store the current state associated with each of the instrument, the location co-ordinate of the surgical kit, and a time stamp when the signal strength of the communication channel is below a predefined threshold and transmitting the current state associated with each of the instrument, the location co-ordinate of the surgical kit and the time stamp via the communication channel when the signal strength of the communication channel exceeds the predefined threshold.

In the embodiment, the deactivation module 316 may deactivate the first set of sensor and the second set of sensors at a start of a surgical kit sterilization i.e. increase of temperature above a predefined threshold, based on monitoring of the temperature surrounding the surgical kit 112. Further, the activation module may activate the first set of sensor and the second set of sensors upon completion of the sterilization i.e. decrease of temperature above a predefined threshold, cycle based on monitoring of the temperature surrounding the surgical kit 112.

In one other embodiment, the deactivation module 316 may generate an alert based on a change in the location co-ordinate of the surgical kit, and the current state. In one example, the deactivation module 316 may generate an alert if the current state of one of the instrument is "absent"; the state of surgical kit is closed state and the location co-ordinate of the surgical kit change over a predefined threshold. In one other example, the deactivation module 316 may generate an alert if the current state of one of the instrument is "absent", the state of surgical kit is closed state and the surgical is in motion for over a predefine time interval.

Exemplary embodiments for tracking one or more instrument in a surgical kit discussed above may provide certain advantages. Though not required to practice aspects of the disclosure, these advantages may include those provided by the following features.

Some embodiments of the device and the method enable power management of the tracking device.

Some embodiments of the device and the method enable battery optimizing.

Some embodiments of the device and the method protection of the first set of sensors and second set of sensors during sterilization process.

Some embodiments of the device and the method enable automated inventory management.

Some embodiments of the device and the method withstand temperature up to 125 degree Celsius in storage condition.

Some embodiments of the device and the method withstand autoclave temperature/pressure conditions due to a sealed mechanical enclosure design.

Some embodiments of the device and the method enable auto shutdown of electronics at high temperature.

Some embodiments of the device and the method support's 2G/3G network for Global Band coverage.

Some embodiments of the device and the method support normal SIM or eSIM based on hardware design.

Figure 4:
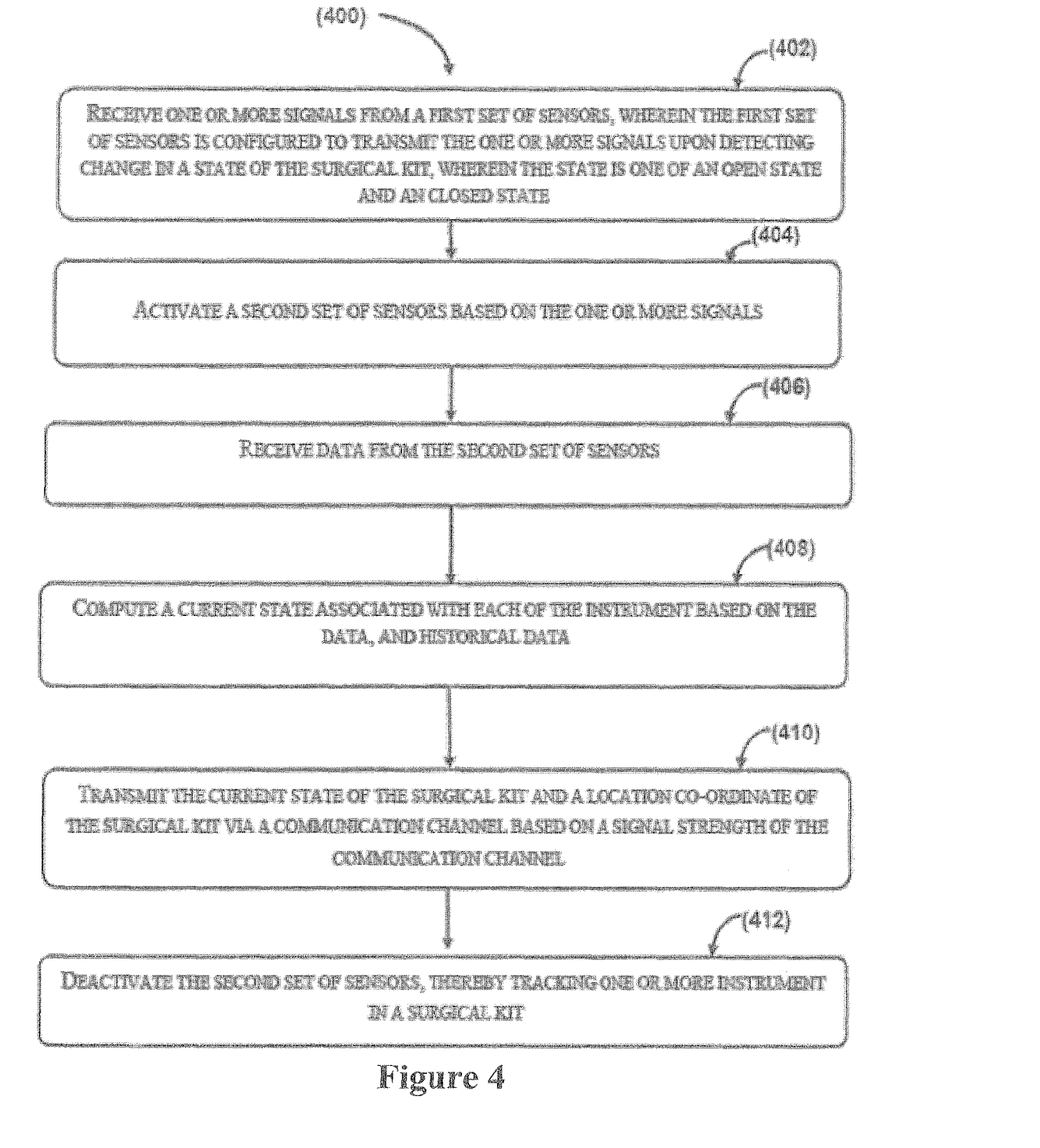
FIG. 4 illustrates a method for tracking one or more instrument in a surgical kit, in accordance with an embodiment of the present subject matter.

Referring now to FIG. 4, a method 400 for tracking one or more instrument in a surgical kit is shown, in accordance with an embodiment of the present subject matter. The method 400 may be described in the general context of computer executable instructions. Generally, computer executable instructions can include routines, programs, objects, components, data structures, procedures, modules, functions, etc., that perform particular functions or implement particular abstract data types.

The order in which the method 400 for tracking one or more instrument in a surgical kit as described is not intended to be construed as a limitation, and any number of the described method blocks can be combined in any order to implement the method 400 or alternate methods. Additionally, individual blocks may be deleted from the method 400 without departing from the spirit and scope of the subject matter described herein. Furthermore, the method can be implemented in any suitable hardware, software, firmware, or combination thereof. However, for ease of explanation, in the embodiments described below, the method 400 may be considered to be implemented in the above-described device 102.

At block 402, one or more signals may be received from a first set of sensors. In one example, the first set of sensors may be configured to transmit the one or more signals upon detecting change in a state of the surgical kit. Further, the state may be one of an open state and a closed state. In one other example, the first set of sensors may comprise one or more of a magnetic sensor, and a motion sensor. In an implementation, the activation module 312 may receive one or more signals from the first set of sensors. Further, the receiving module 312 may store the one or more signals in the system data 320.

At block 404, a second set of sensors may be activated based on the one or more signals. In an implementation, the activation module 312 may activate the second set of sensors and store the activation data in system data 320.

At block 406, data may be received from the second set of sensors. In one example, the data may be associated with one or more instruments within the surgical kit. In the implementation, the deactivation module 314 may receive data from the second set of sensors and store the data in the system data 320.

At block 408, a current state associated with each of the instrument may be computed based on the data, and historical data. In one example, the current state may be one of present in the surgical kit or absent in the surgical kit. In the implementation, the deactivation module 314 may compute a current state associated with each of the instrument based on the data and historical data. Further, the deactivation module 314 may store current state in the system data 320.

At block 410, the current state of the surgical kit, the current state associated with each of the instrument and a location co-ordinate of the surgical kit may be transmitted via a communication channel based on a signal strength of the communication channel. In the implementation, the deactivation module 314 may transmit the current state of the surgical kit, the current state associated with each of the instrument and a location co-ordinate of the surgical kit, and may store the transmitted data in the system data 320.

At block 412, the second set of sensor may be deactivated, thereby tracking one or more instrument in a surgical kit. In the implementation, the deactivation module 314 may deactivate the second set of sensors once the transmission is complete.

Exemplary embodiments discussed above may provide certain advantages. Though not required to practice aspects of the disclosure, these advantages may include a method and device for tracking one or more instrument in a surgical kit. Although implementations for methods and device for tracking one or more instrument in a surgical kit have been described in language specific to structural features and/or methods, it is to be understood that the appended claims are not necessarily limited to the specific features or methods described. Rather, the specific features, devices, systems and methods are disclosed as examples of implementations for tracking one or more instrument in a surgical kit.

We claim:

1. A device for tracking one or more instrument in a surgical kit, the device comprising:
   a magnetic sensor, wherein the magnetic sensor is configured to transmit one or more signals upon detecting a change in a state of a surgical kit, wherein the state is one of an open state and a closed state;
   one or more of a load cell and a Piezo sensor, wherein the one or more of the load cell and the Piezo sensor are activated based on the one or more signals; and
   a machine control unit coupled to the magnetic sensor and the one or more of the load cell and the Piezo sensor, wherein the machine control unit is capable of executing instructions to perform steps of:
      receiving the one or more signals from the magnetic sensor;
      activating the one or more of the load cell and the Piezo sensor based on the one or more signals;
      receiving data from the one or more of the load cell and the Piezo sensor, wherein the data is associated with one or more instruments within the surgical kit;
      computing a current state associated with each of the one or more instruments based on the data, and historical data, wherein the current state is one of: instrument present, instrument absent, and instrument present in reduced quantity;
      transmitting the current state of the surgical kit, the current state associated with each of the one or more instruments and a location co-ordinate of the surgical kit via a communication channel based on a signal strength of the communication channel; and
      deactivating the one or more of the load cell and the Piezo sensor, thereby tracking one or more instruments in the surgical kit.

2. The device of claim 1, wherein the machine control unit is further capable of executing instructions to perform steps of:
   deactivating at least the magnetic sensor and the one or more of the load cell and the Piezo sensor at a start of a surgical kit sterilization; and
   activating the magnetic sensor and the one or more of the load cell and the Piezo sensor upon completion of the sterilization cycle.

3. The device of claim 1, wherein the machine control unit is further capable of executing instructions to perform steps of:
   storing the current state associated with each of the one or more instruments, the current state of surgical kit, the location co-ordinate of the surgical kit, and a time stamp when the signal strength of the communication channel is below a predefined threshold; and
   transmitting the current state associated with each of the one or more instruments, the current state of the surgical kit, the location co-ordinate of the surgical kit and the time stamp via the communication channel when the signal strength of the communication channel exceeds the predefined threshold.

4. The device of claim 1, wherein the machine control unit is further capable of executing instructions to perform step of computing a total usage time of the instrument based on the current state and the historical data.

5. The device of claim 1, wherein the machine control unit is further capable of executing instructions to perform step of generating an alert based on a change in the location co-ordinate of the surgical kit, and the current state.

6. A method for tracking one or more instruments in a surgical kit, the method comprising:
   receiving, by a machine control unit, one or more signals from a magnetic sensor, wherein the magnetic sensor is configured to transmit the one or more signals upon detecting a change in a state of the surgical kit, wherein the state is one of an open state and an closed state;
   activating, by the machine control unit, a one or more of a load cell, and a Piezo sensor based on the one or more signals;
   receiving, by the machine control unit, data from the one or more of the load cell, and the Piezo sensor, wherein the data is associated with one or more instruments within the surgical kit;
   computing, by the machine control unit, a current state associated with each of the one or more instruments based on the data, and historical data, wherein the current state is one of: instrument present, instrument absent, and instrument present in reduced quantity;
   transmitting, by the machine control unit, the current state of the surgical kit, the current state associated with each of the one or more instruments and a location co-ordinate of the surgical kit via a communication channel based on a signal strength of the communication channel; and
   deactivating, by the machine control unit, the one or more of the load cell, and the Piezo sensor, thereby tracking one or more instrument in a surgical kit.

7. The method of claim 6, further comprising:
   deactivating, by the machine control unit, at least the first magnetic sensor and the one or more of the load cell, and the Piezo sensor at a start of a surgical kit sterilization; and
   activating, by the machine control unit, the magnetic sensor and one or more of the load cell, and the Piezo sensor upon completion of the sterilization cycle.

8. The method of claim 6, further comprising:
   storing, by the machine control unit, the current state associated with each of the one or more instruments, the current state of the surgical kit, the location co-ordinate of the surgical kit, and a time stamp when the signal strength of the communication channel is below a predefined threshold; and
   transmitting, by the machine control unit, the current state associated with each of the one or more instruments, the current state of the surgical kit, the location co-ordinate of the surgical kit and the time stamp via the communication channel when the signal strength of the communication channel exceeds the predefined threshold.

9. The method of claim 6, further comprising computing, by the machine control unit, a total usage time of the one or more instruments based on the current state and the historical data.

10. The method of claim 6, further comprising generating, by the machine control unit, an alert based on a change in the location co-ordinate of the surgical kit, and the current state.

\* \* \* \* \*

UNITED STATES PATENT AND TRADEMARK OFFICE
CERTIFICATE OF CORRECTION

PATENT NO. : 10,390,902 B2  
APPLICATION NO. : 16/010285  
DATED : August 27, 2019  
INVENTOR(S) : Lalit Kumar Singh and Pankaj Gupta It is certified that error appears in the above-identified patent and that said Letters Patent is hereby corrected as shown below:

In the Claims

Claim 7, Column 10, Line 42 "at least the first magnetic" should be --at least the magnetic--

Signed and Sealed this  
Twenty-eighth Day of January, 2020

Andrei Iancu  
*Director of the United States Patent and Trademark Office*